(12) United States Patent
Reusch et al.

(10) Patent No.: US 6,179,612 B1
(45) Date of Patent: Jan. 30, 2001

(54) FAST TRANSFER YOKE

(75) Inventors: Diether Reusch, Westerburg; Rudolf Cramer, Sachsenkam, both of (DE)

(73) Assignee: Synthese Dentale Forschungs-Und Entwickseungsgedsellschaft MBH, Westerburg (DE)

( * ) Notice: Under 35 U.S.C. 154(b), the term of this patent shall be extended for 0 days.

(21) Appl. No.: 09/436,606

(22) Filed: Nov. 9, 1999

(30) Foreign Application Priority Data

Nov. 9, 1998 (DE) .............................................. 198 51 443

(51) Int. Cl.⁷ .................................................. A61C 19/04
(52) U.S. Cl. .................................................. 433/76; 433/69
(58) Field of Search ................................ 433/56, 68, 69, 433/73

(56) References Cited

U.S. PATENT DOCUMENTS

| | | | |
|---|---|---|---|
| 3,078,584 | * | 2/1963 | Cohn ........................................ 433/73 |
| 4,126,938 | * | 11/1978 | Lee ......................................... 433/73 |
| 4,537,574 | * | 8/1985 | Clark ....................................... 433/69 |
| 4,681,539 | * | 7/1987 | Knap ....................................... 433/73 |
| 4,892,480 | * | 1/1990 | Levandoski ............................. 433/73 |
| 4,909,737 | * | 3/1990 | Lee ......................................... 433/73 |
| 5,176,515 | * | 1/1993 | Andrews ................................. 433/73 |
| 5,738,517 | * | 4/1998 | Keller ..................................... 433/73 |

* cited by examiner

Primary Examiner—Ralph A. Lewis
(74) Attorney, Agent, or Firm—Brooks & Kushman P.C.

(57) ABSTRACT

The invention concerns a fast transfer yoke for the cranium-calculated transfer of a maxilla plaster model from a patient into a dental articulator as well as for the recording of axis-related individual mandibular joint geometry of the patient in question.

The invention is to create a fast transfer yoke that, with easy handling, facilitates fast recording of patient data, i.e., of the mandible movements as well as of the patient axis and their transfer into a dental articulator or to an mounting apparatus.

The invention is characterized in that the flag yoke (1) is strapped against the posterior wall of the acoustic meatus and/or against the glabella or forehead support (51); in that flags (2) are each attached to a end piece (7) that is detachably attached to the flag yoke (1); in that on each flag (2) an angular plate (27) is located that is angularly adjustable and detachably lockable; in that the write heads (22, 22a) can be positioned both on the flag (2) and on the angular plate (27) and in that to the side of each flag (2) a centering tip (20) can be positioned in an assumed or actual patient axis. (FIG. 1).

20 Claims, 11 Drawing Sheets

FAST TRANSFER YOKE

The invention concerns a fast transfer yoke for the cranium-calculated [unconfirmed translation] transfer of a plaster model of the maxilla from a patient into a dental articulator as well as for the recording of the axis-related individual geometry of the mandibular joint of the patient in question containing a flag yoke with flags located near the mandibular joints and earplugs or ear supports and a glabella support for the local fixation on the head and a recording yoke to which an occlusion fork is attached for the actuation of the write heads on the recording yoke for the recording of the sagittal movement of the hinge axes.

These types of fast transfer yokes of conventional design (e.g., DE 42 11 016 A1, DE 42 11 018 A1) are characterized in that they are not capable of meeting both requirements simultaneously, i.e., the cranium-calculated transfer of the plaster model of the maxilla and the recording of the axis-related individual geometry of the mandibular joint. Usually so-called "Quick Mount Yokes" are based on an arbitrary hinge axis. The advantage here lies in the easy and fast handling. The disadvantage resides in the fact that an axis-related geometry of the mandibular joint cannot be recorded.

Several fast transfer yokes are adjusted from the outside to arbitrary axis points, others are anchored in the foramen and braced at the front with a glabella support.

In this mode of attachment to the cranium, the earplugs collide with the anatomical posterior mandibular joint supports, permitting the transfer yoke to shift in relation to the cranium if the mandible conducts pro-, medio- or laterotrusive movements. This makes the recording of axial movements of the mandible impossible.

For the recording of the movements of the mandible, the patient ordinarily first conducts a protrusive and retrusive movement. The recording styli that are attached to the recording yoke record the sagittal movement that occurs and the joint path inclination (HKN [expansion unknown; perhaps, main condylar inclination]).

In order to determine the Bennett movement, the mandible is moved to the right and to the left. The lateral offset of the mandible is recorded by the change in distance of the recording styli vs. the flags.

By way of example, the Bennett movement can be recorded by means of an indicating caliper, whereas the distance of the path of the joint movement needs to be read from the indicating caliper. The value pairs read are calculated into a Bennett curve by way of conversion tables.

Because of the multitude of process steps required, it is desirable to achieve a simplification and at the same time an increase in precision of the three-dimensional joint movement recording.

Therefore, the invention is based on the problem of developing a fast transfer yoke that, with easy handling, facilitates a fast recording of patient data, i.e., of the movements of the mandible and of the patient axis and their transfer into a dental articulator or mounting apparatus.

DISCLOSURE OF INVENTION

The problem on which the invention is based is solved for a fast transfer yoke of the aforementioned type in that the flag yoke is tensioned by spring force against the posterior wall of the acoustic meatus and/or the glabella or frontal support, in that the flags are each attached to an end piece that is detachably attached to the flag yoke, in that to each flag an angular plate is detachably attached that can be adjusted at various angles, in that the write heads can be positioned both on the flag and on the angular plate and in that to the side of each flag a centering tip can be positioned in an assumed or actual patient axis.

In this manner a three-dimensional recording can be conducted with the fast transfer yoke of the movements of the mandible, such as the HKN paths and the Bennett movement, without the need for any additional measuring devices. This means that the fast transfer yoke is suited for all types of measurements. This significantly reduces the effort and simultaneously improves the precision of the recording. By way of the centering tips that can be positioned next to the flags after determination of the patient axis and after removal of the end pieces from the legs of the fast transfer yoke, in addition it can be transferred to a dental articulator or a mounting apparatus in a simple manner.

In order allow the writing tips or the centering tips to be adjusted to an arbitrary patient axis, the flags each feature an axis bore. This makes it easier to fit the recording yoke to the patient and facilitates the positioning of the transfer yoke on an mounting apparatus or articulator with centering tips.

For the easy positioning of the centering tips next to the flags, a continuation of the invention is characterized in that mounting devices can be attached to the flag yoke that feature the centering tips that can be positioned on the flags, whereas the centering tip is inserted into a carrier that can be longitudinally shifted and locked in a fixed position on the mounting device.

Preferably, the angular plate is connected with the flag by way of a clamping device permitting its very easy adjustment to the axis point and according to the mandibular joint path inclination.

The clamping device consists of a pressure plate that is flush with the angular plate and of a rotatable clamping jaw that is positioned at a distance to and connected with the pressure plate, whereas the clamping jaw can be swiveled in the direction of the pressure plate against a spring force.

In a further configuration, the angular plate can be connected with the flag by way of a magnetic mount.

The angular plate can also be attached directly to the arms of the flag yoke or to its end pieces.

In a continuation of the invention, the lateral arms of the recording yoke are configured so as to make the write heads interchangeable. In this configuration the write heads are designed in such a way that once the recording yoke is adjusted to the axis it does not need to be readjusted for the HKN and the Bennett recordings. In this fashion, a direct three-dimensional recording of the mandibular movements can be made. In lieu of the described mechanical recording of the path of the joint movement it is certainly possible to apply an electronic recording of the path of the joint movement.

Because of the change of the flag/writing tip distance during lateral movements, it is necessary that the mechanical or electrical writing tips are spring mounted.

In a continuation of the invention, the front end of the flag yoke is additionally equipped with a fixture for the retention of a writing plate, which can be touched by a recording stylus that is adjustably attached to the occlusion fork handle. In this way the mandibular movements, i.e., the movements of the front teeth can be recorded in an easy manner and, with the help of these recordings, the dental articulator can be adjusted so that it reproduces the mandibular movements accurately.

Another configuration of the invention is additionally characterized in that frontal supports can be attached to the flag yoke. Their function is added stabilization of the flag yoke on the forehead against inadvertent movements. These frontal supports are indispensable in the event that the flag end pieces with earplugs are exchanged against flag end pieces for ear saddle [unconfirmed translation] support.

Additionally, flattened earplugs can be used that are flattened in the direction of the glabella support, creating a clearance for the mandible and giving the patient some relief.

In such cases where, due to patient conditions, earplugs cannot be used to fasten the flag yoke, one embodiment of the invention provides for ear saddle support in lieu of earplugs that, by way of vertical supports, are attached to an end piece that pertains to each of the lateral legs of the flag yoke.

The end pieces are preferably attached to each of the legs in a way that allows them to be interchanged.

In one continuation of the invention a flag is attached to each of the end pieces for mechanical or electronic recording of the joint movement path.

In order to facilitate optimal adjustability to the anatomical conditions, the vertical arm is designed to be height-adjustable.

Below, the invention is explained in more detail based on an embodiment example with reference to individual figures. These figures show.

BRIEF DESCRIPTION OF DRAWINGS

BEST MODE FOR CARRYING OUT THE INVENTION

Figure 1:
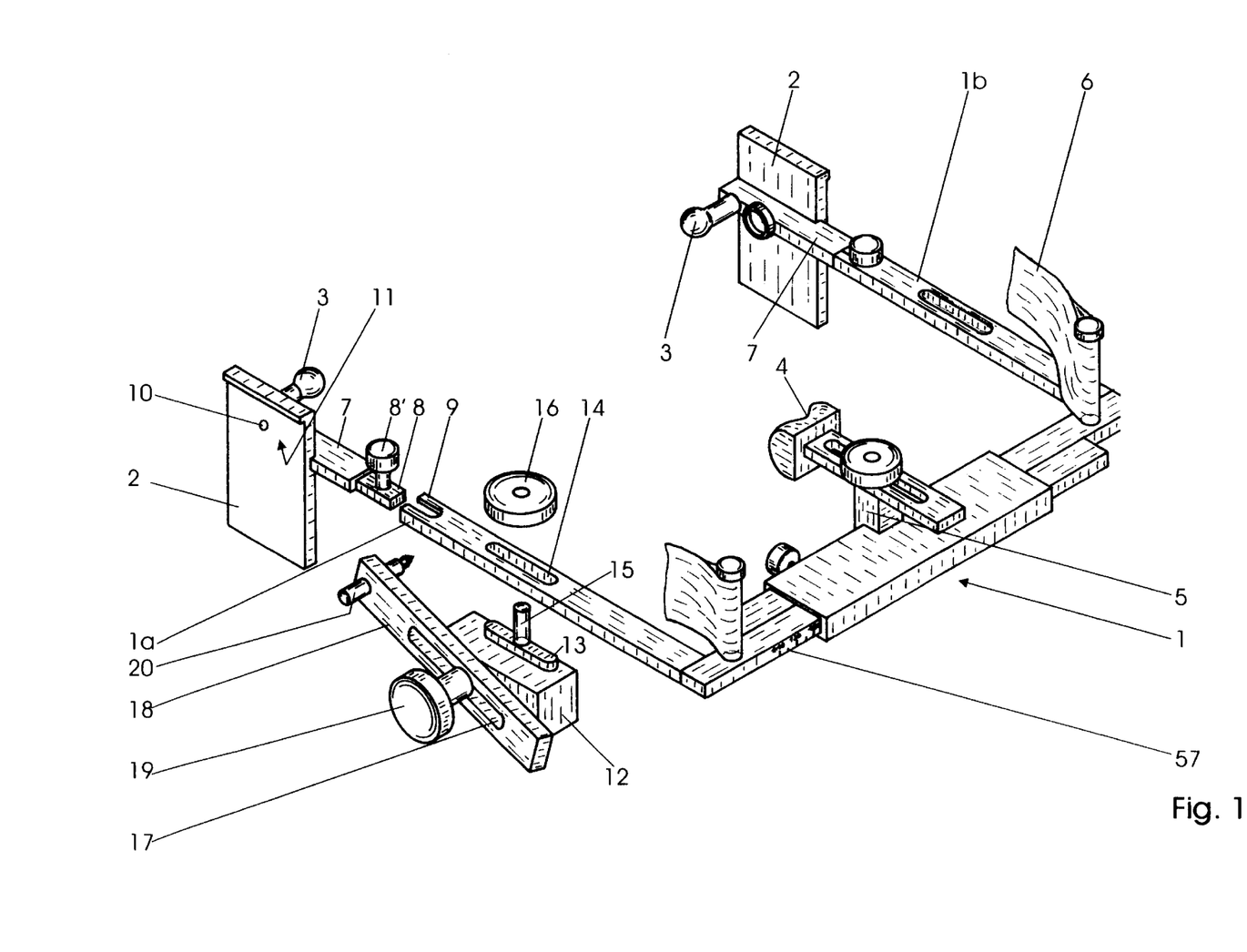
FIG. 1, a fast transfer yoke for the determination of patient data and for their transfer to a dental articulator.
Figure 2:
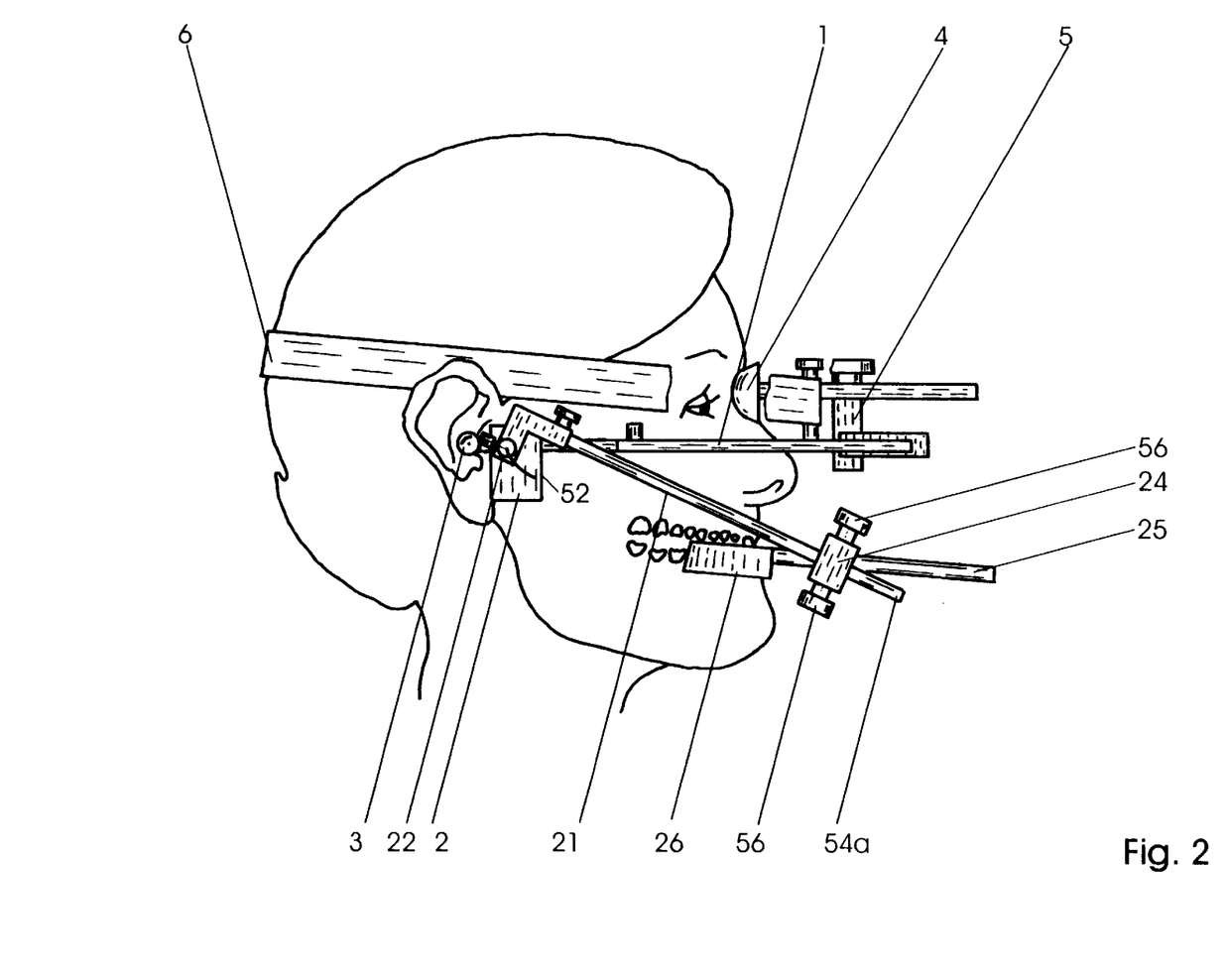
FIG. 2, the fast transfer yoke that is attached to the cranium by means of a rubber band for the recording of the protrusive and retrusive movements based on an orbital hinge axis.
Figure 3:
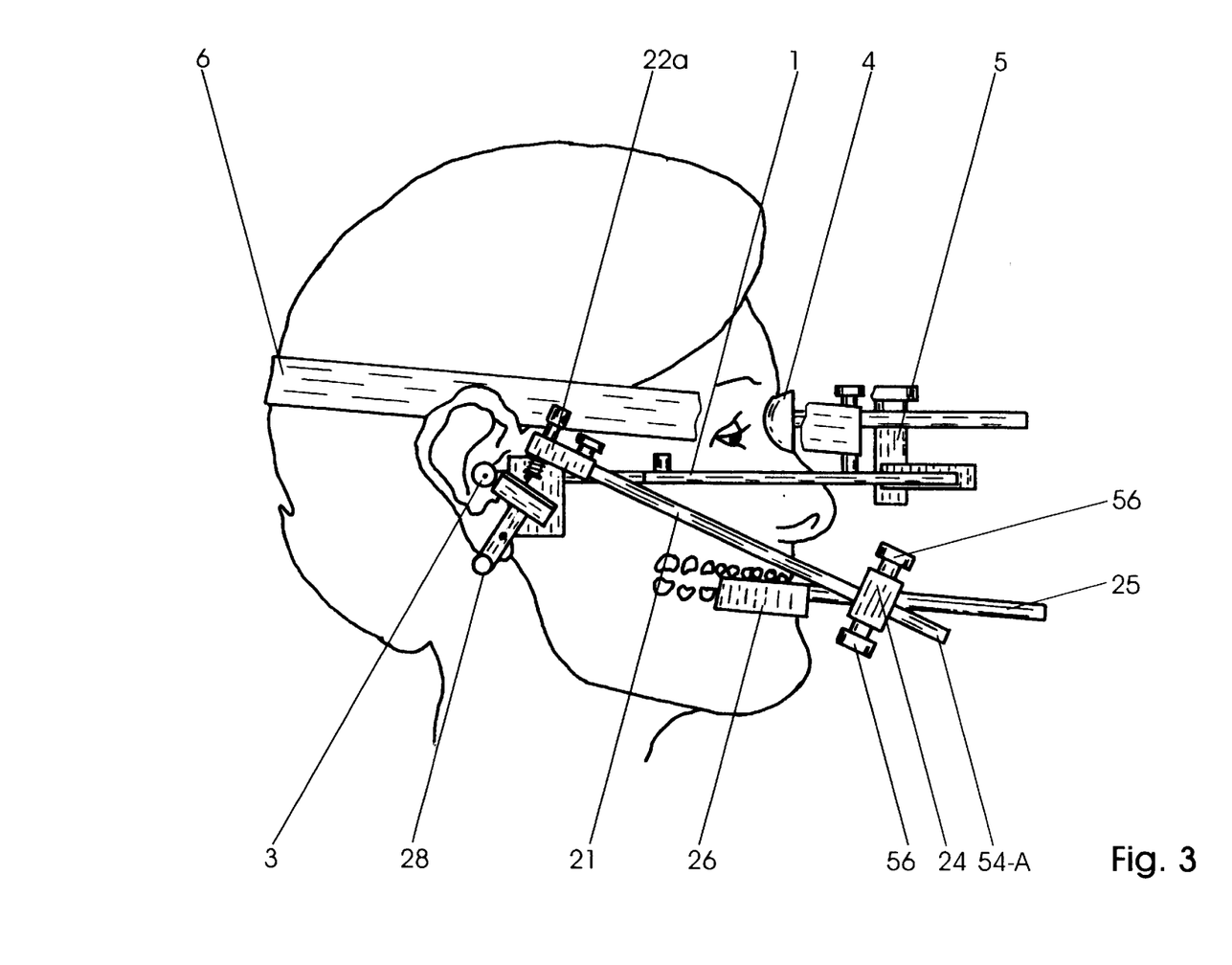
FIG. 3, the fast transfer yoke according to FIG. 1 with an angular plate for the recording of Bennett movements based on an orbital axis point.

In FIGS. 1–3, a recording device can be seen that consists of a flag yoke 1 that is stationarily attached to the cranium of the patient and can be width-adjusted and the pertinent sagittal flags 2 for the recording of the mandibular movements. In addition a scale 57 is provided at the bottom of the flag 1 that indicate the distance of the earplugs 3 and that is required for the preadjustment of an mounting apparatus or of an articulator.

The flag yoke 1 is attached to the cranium with earplugs 3 that protrude from the lateral arms of the flag yoke 1 and that are to be inserted into the porus acusticus. In addition, an adjustable glabella support 4 is provided that is located in front of the cranium and attached to the flag yoke 1 via a detachable carrier 5. In lieu of the earplugs 3 (FIG. 1), flattened earplugs 31 (FIG. 4) can be used. The earplugs 31 are flattened in the direction of the glabella support 4.

In order to achieve that the mandibular joint can be freely moved and is not restricted by the earplugs, the flag yoke 1 is strapped against the cranium and/or the glabella by means of a rubber band 6. In order to avoid recording mistakes caused by projections, the flags 2 are positioned as close as possible to the sides of the mandibular joints.

The flags 2 and the pertinent earplugs 3 are attached to an end piece 7 that can be positioned on the lateral legs [sic; inconsistent use of "arms" and "legs"] 1a and 1b of the flag yoke 1. For this purpose an adapter piece 8 protrudes from the end piece 7 that can be inserted into a corresponding recess in the legs 1a,1b. The positioning is accomplished by means of a set screw 8', the shaft of which can be engaged in a fork 9 in the legs 1a,1b.

Flag 2 also features an axis bore 10 in an orbital position of the patient axis. This axis bore serves for the transfer of the patient axis to a dental articulator when less accuracy is demanded. If high accuracy is demanded, the precise axis point 11 must first be determined, which is then used for the setting of the dental articulator. How to precisely determine this axis point 11 is described later based on FIG. 11.

FIG. 1 also shows a mounting device 12 for the transfer of the individual patient axis to a dental articulator that can be attached to the legs 1a,1b. For this purpose a molded piece 13 is located on the mounting device 12 that is of identical shape as a groove 14 in the arms 1a,1b. The positioning of the mounting device 12 on the arm 1a,1b is accomplished by means of a threaded pin 15 in connection with a set screw 16.

Also provided on the side of the mounting device 12 is a carrier 18 that can be longitudinally adjusted in a groove 17, which [carrier] can be locked in place on the mounting device 12 with the aid of a set screw 19. The carrier 18 serves as the retainer of a centering tip 20 that can be optionally centered either in the axis bore 10 or in the axis point 11 depending on the desired precision of the setting of the dental articulator.

After centering the centering tip 20, the end piece 7 with the flag 2 and the earplug 3 just needs to be removed and the transfer yoke can be attached to the mounting apparatus.

The HKN path 52 (protrusive movement) is recorded by means of a recording yoke 21 that consists of lateral arms 54 or lateral arms 54-A that are connected with the occlusion fork handle 25 by the clamps 24 and set screws via the cross rod 48. On the flag-side ends of the lateral arms 54 or 54-A write heads 22 with recording styli 23 are located that are oriented on the flags 2 bilaterally along the bore 10. The recording yoke 21 is connected in the middle of the recording yoke 21 on the cross rod 48 by means of a clamp (not shown) with the occlusion fork handle 25.

When the jaw conducts movements in a protrusive and retrusive direction it causes the preferably spring mounted recording stylus 23 on the flag 2 to move and thus to record the mandiblery movement.

For the direct recording of the Bennett movement, an angular plate 27 is provided that can be attached to the flag 2. This angular plate 27 can be oriented toward axis point X on the flag 2 according to the natural joint path inclination. Details of the angular plate 27 can be seen in FIGS. 4 and 5.

Figure 4:
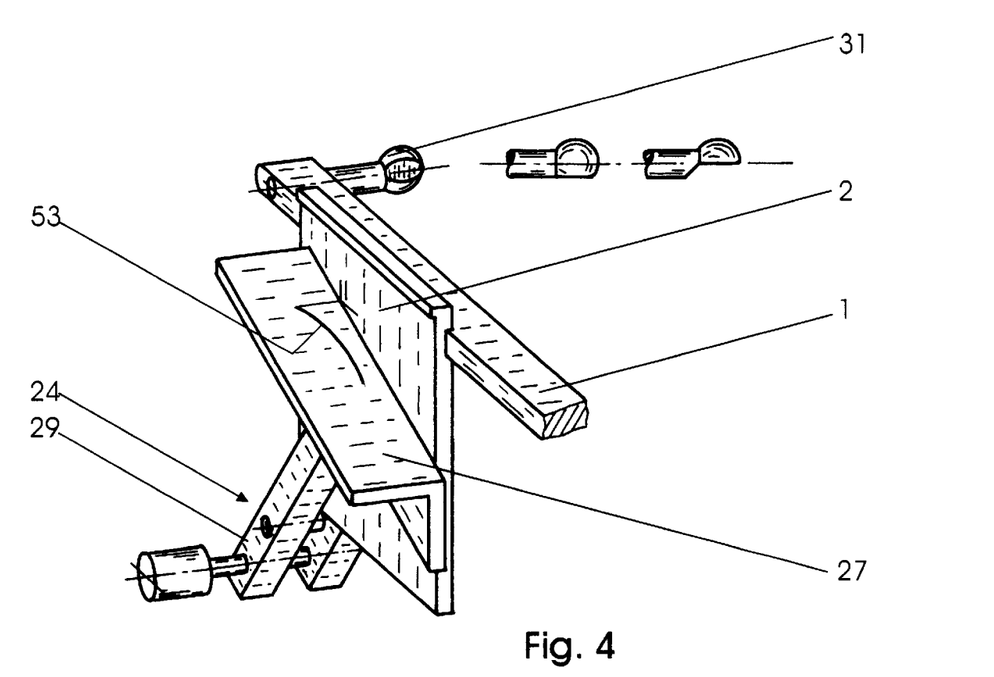
FIG. 4, an angular plate that is attached to the flag yoke of the fast transfer yoke.
Figure 5:
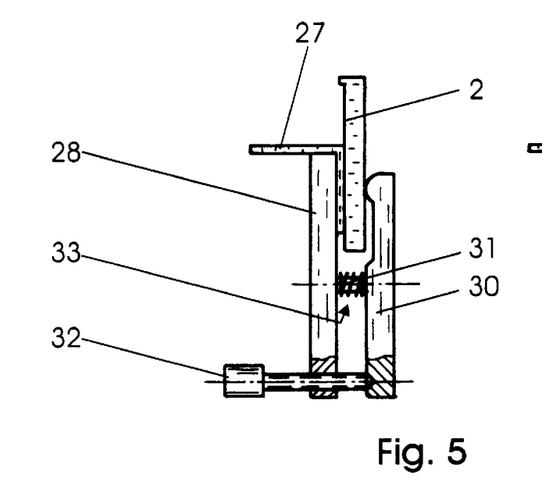
FIG. 5, frontal view according to FIG. 4.

The angular plate 27 is connected with the flag 2 via a clamping device 28. This clamping device 28 consists of a pressure plate 29 that sits flush against the angular plate 27 and of a clamping jaw 30 that is connected with the pressure plate 29 and can be swiveled. The clamping jaw 30 is attached to a support 31 and can be swiveled and it is put under tension by means of a pressure screw 32. In order to be able to push the angular plate 27 on to the flag 2 with greater ease, the pressure plate 29 and the clamping jaw 30 are kept apart, e.g., by means of a pressure spring.

Figure 6:
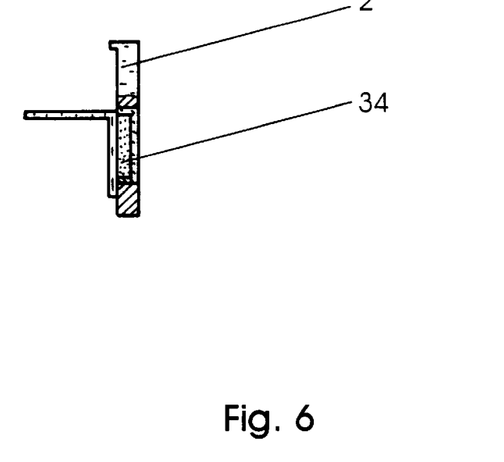
FIG. 6, a flag featuring a magnetic mount for the retention of the angular plate.

Another possibility to attach the angular plate 27 securely to the flag 2 consists in the use of a magnetic mount 34 (FIG. 6).

Figure 7:
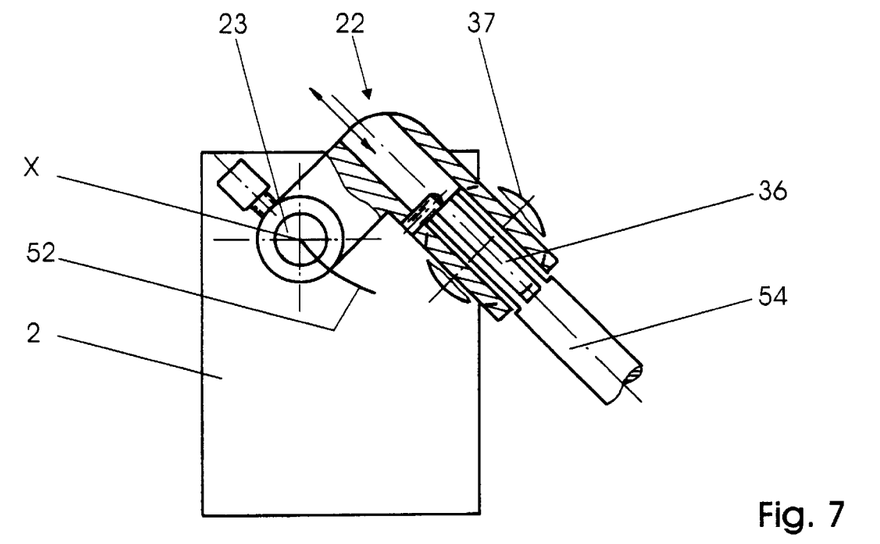
FIG. 7, a lateral arm 31 adjusted to the axis point X with a write head 22 for joint path recording (HKN)
Figure 8:
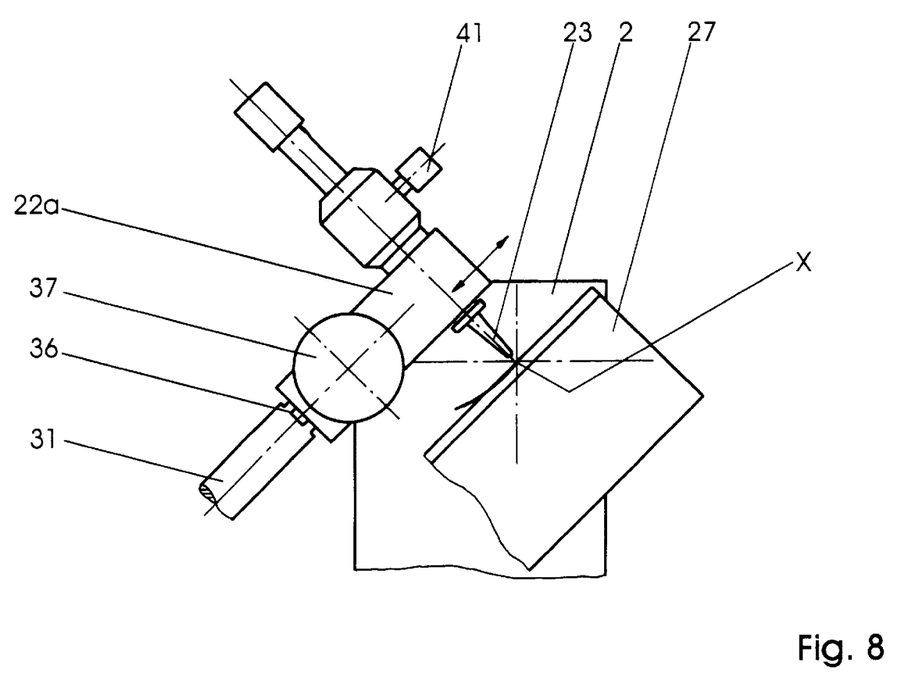
FIG. 8, a lateral arm 31, the adjustment of which is unchanged as compared to FIG. 7, with an angular plate 27 and a write head 22A for the Bennett path 53, with the writing tip automatically hitting axis point X.

For the recording of the lateral or Bennett movement on the angular plate 27 the write head 22 for the HKN joint path must be removed from the rear end of the lateral arm 54 or 54-A. The write head 22a for the Bennett movement is attached to the rear end of the lateral arm 54 or 54-A (FIGS. 7, 8). The write head 22,22a is attached, e.g., by means of a square prism 36 in connection with a set screw 37. The basic setting with regard to the axis point X is preserved.

FIG. 8 shows a lateral arm 54 that is unchanged as compared to FIG. 7 with an angular plate 27 and the write head 22a for the recording of the Bennett joint path 53 (FIG. 4), whereas the writing tip automatically hits axis point X.

Figure 9A:
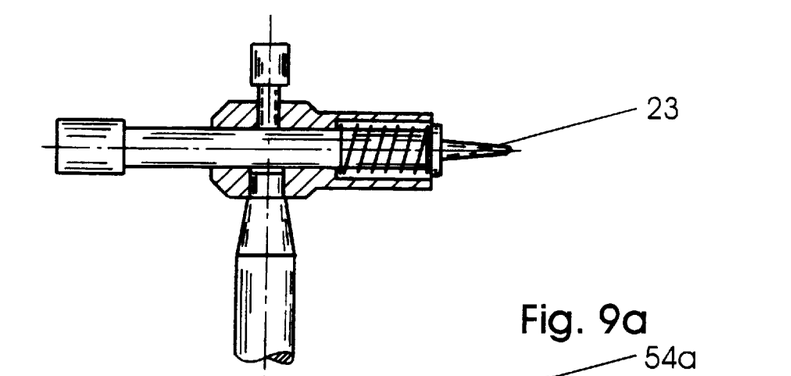
FIG. 9a, a detail view of the write head with spring cushioned writing tip.
Figure 9B:
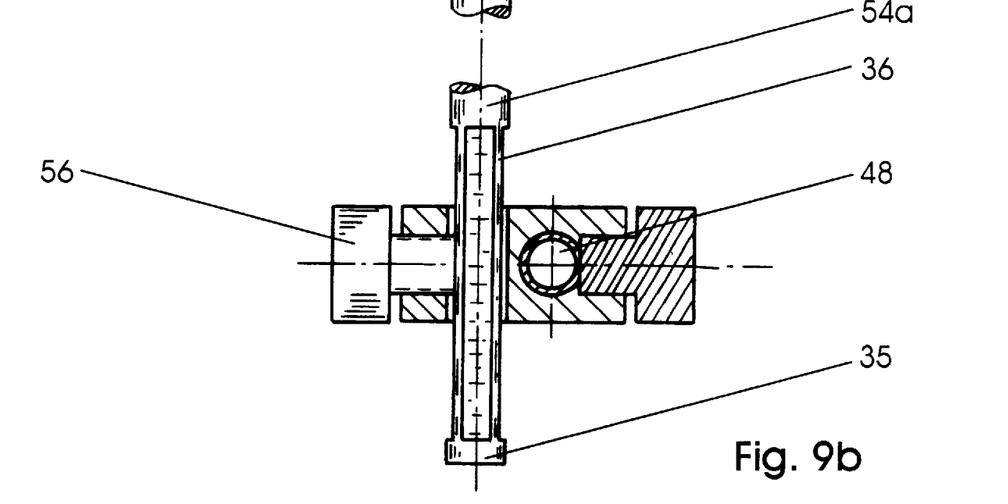
FIG. 9b, square prism guide for the write head according to FIGS. 6, 7.
Figure 9C:
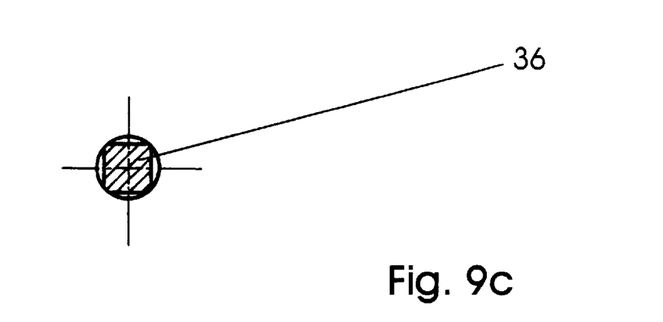
FIG. 9c, a top view of the square prism guide.

The ends of the lateral arms 54,54-A are preferably configured in such a manner that the write heads 22 and 22a are attached over one or more surfaces (FIGS. 9a–9c). This guarantees a very secure and flawless positioning of the write head 22 or its writing tip 23 either above the flag 2 or above the angular plate 27. In addition, a particularly play-free guiding action is guaranteed by the square prism 36.

Figure 10:
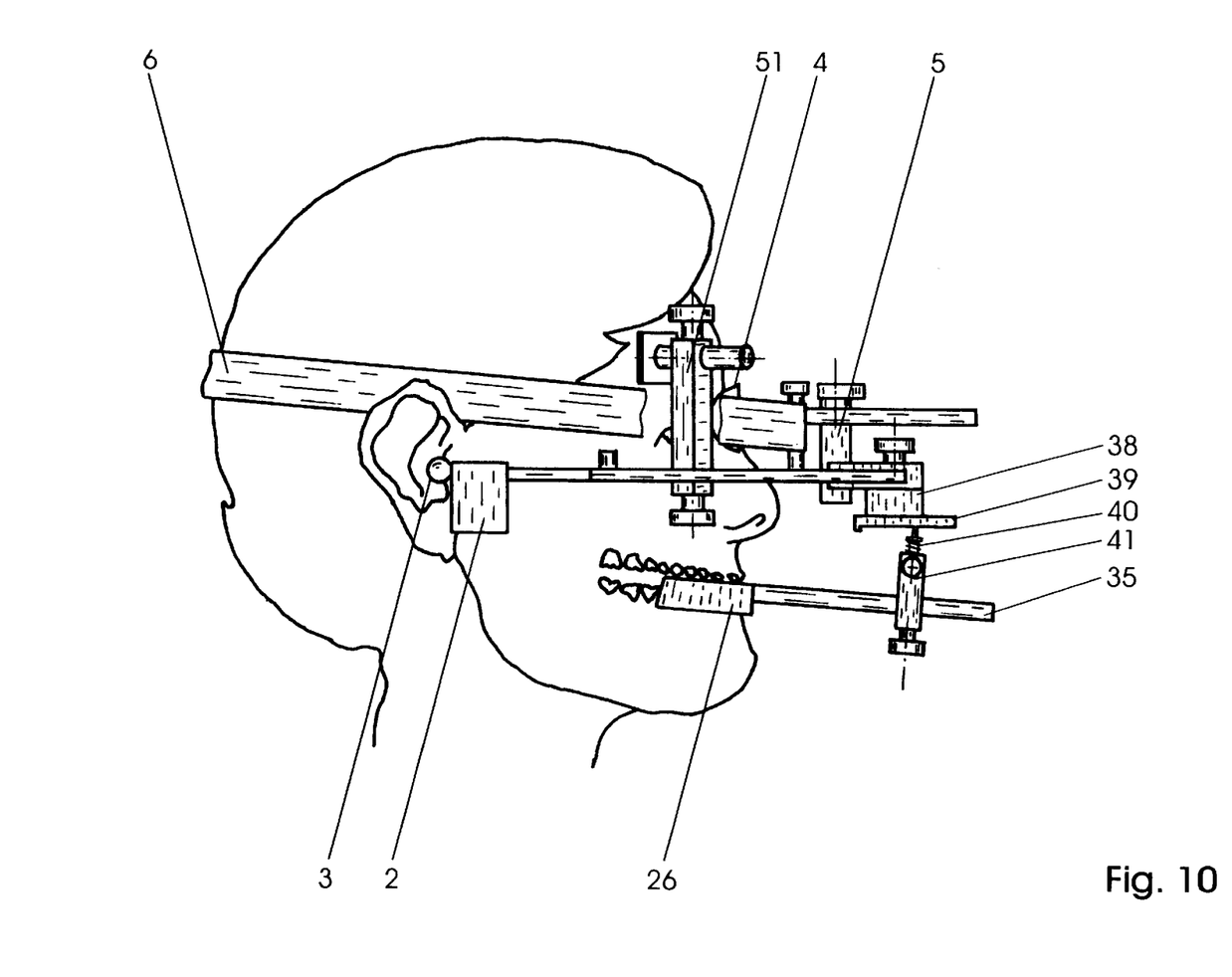
FIG. 10, the fast transfer yoke with a recording device according to FIGS. 3, 4, with writing plate for the recording of the mandibular movements in the front tooth area.

For the recording of the complete mandibular movement, i.e., the movement of the front teeth, furthermore, an attachment 38 is provided at the front end of the flag yoke 1 for the retention of a writing plate 39. Upon this writing plate 39 a springy recording stylus 40 can be set down that is adjustably attached to the handle 25 of the occlusion fork 26 by means of a clamp 41 (FIG. 10). In lieu of the recording stylus 40, of course, the write head 22,22a (FIGS. 7, 8) can be attached to the handle 25 of the occlusion fork 26.

Figure 13:
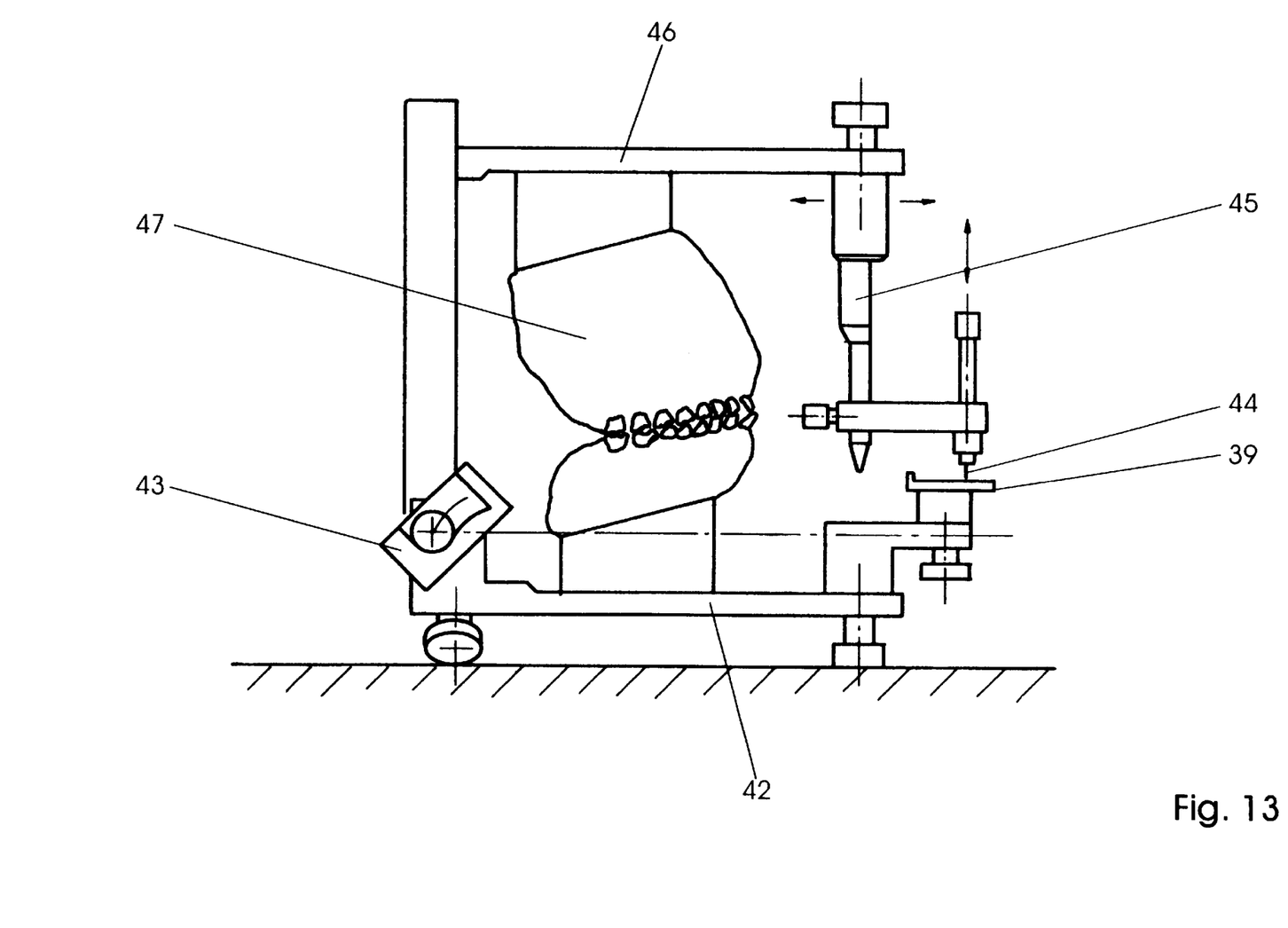
FIG. 13, a dental articulator with writing plate inserted according to FIG. 8 in the setting position (upside down) and with a moveably attached indicator.

In this manner, mandibular movements, i.e., the movements of the front teeth can be readily recorded, and with the help of these recordings a dental articulator can be set in such a manner that it precisely reduplicates the mandibular movements. For this purpose, the writing plate 39 is attached solely to the top part 42 of the dental articulator instead of to the otherwise used incisal table. In FIG. 13 such a dental articulator is shown that, for the purpose of adjusting the condylar joints 43, has been placed upside down so that by means of a moveable indicator 44 that is attached to the incisal pin 45 a comparison is possible of the front tooth movement (FIG. 10) that has previously been recorded on the patient with the movement of the bottom part 46, or the dental articulator can be adjusted via the condylar joints 43. The condylar joint 43 and the plaster model 47 of the maxilla and mandible that is installed in the dental articulator have here been drawn only schematically.

Figure 11:
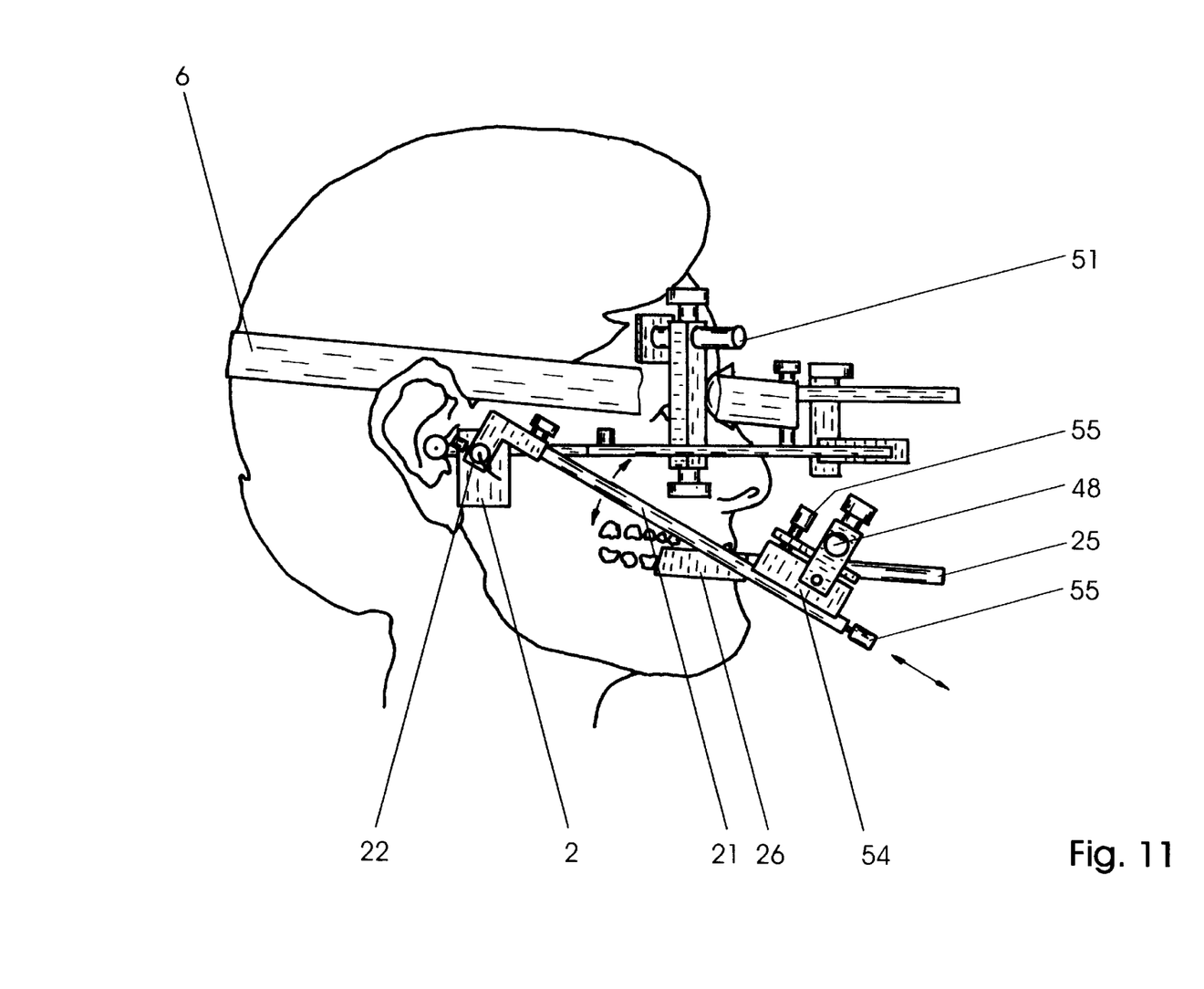
FIG. 11, the fast transfer yoke attached to the cranium by means of a rubber band with an additional forehead support and with lateral arms for the determination of the precise patient axis that are individually adjustable by way of adjusting screws.

If a particularly accurate transfer of patient data is desired, the patient axis can be determined with precision according to FIG. 11. For this purpose a forehead support 51 is first mounted on the flag yoke 1. Subsequently the occlusion fork 26 is attached to the mandible and connected to the lateral arm 54 via the handle 25 and the cross strut 48. If the patient opens the mandible, the write head 22 conducts a movement on the flag 2. The adjustable lateral arms 54 must now be adjusted by means of the adjusting screws 55 by way of longitudinal or pivoting movements until the write head 22 no longer conducts a movement relative to the flag 2. This determines the precise patient axis.

Figure 12:
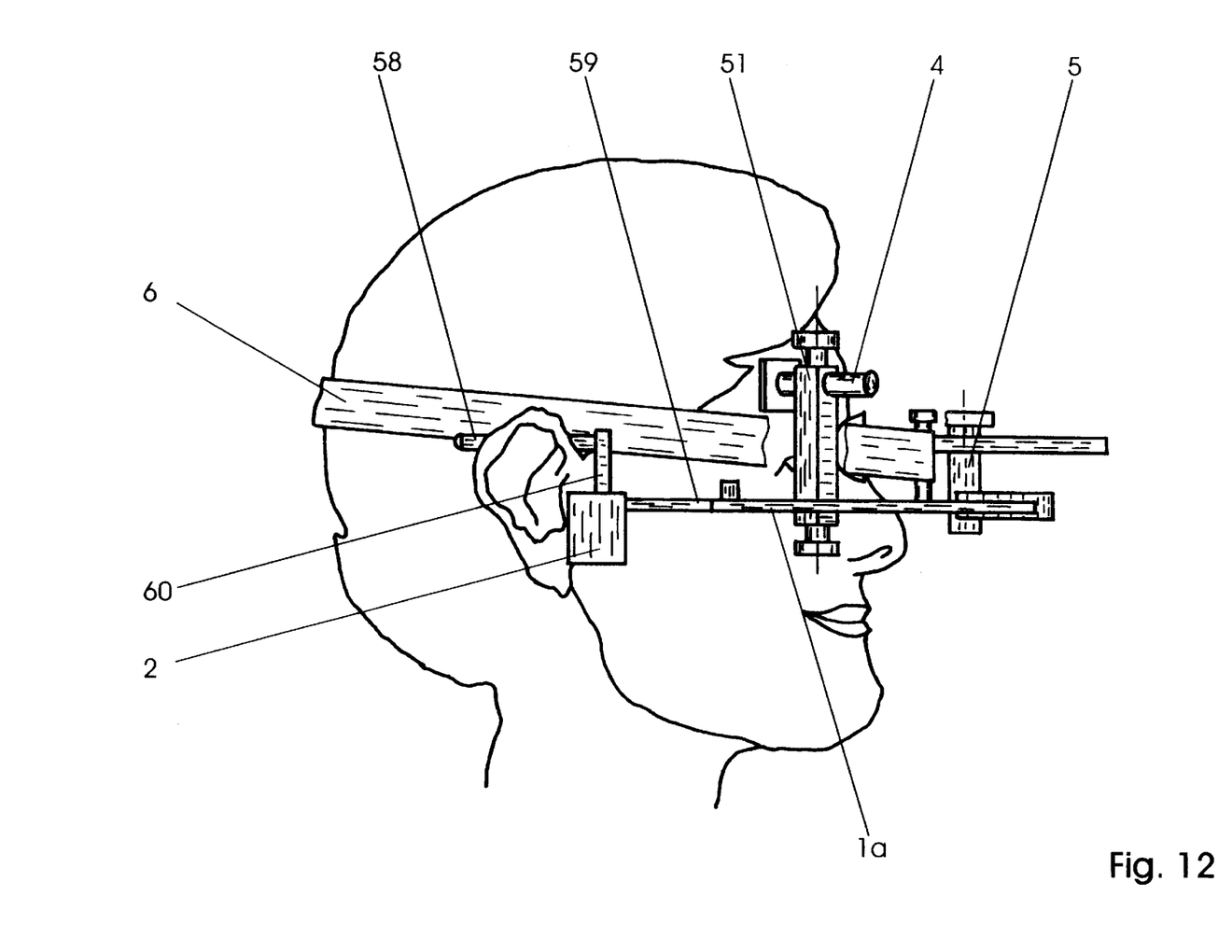
FIG. 12, a fast transfer yoke with ear saddle supports in lieu of earplugs.

In FIG. 12 a special variant of the transfer yoke is shown in which ear saddle support is provided that replaces the otherwise required end pieces 7 with the earplugs 3 with an end piece 59 for the ear saddle supports 58. To this end piece 59 a flag 2 can be attached for the mechanical or electronic joint path recording. The ear saddle supports 58 are each attached by way of vertical supports 60 to one of the lateral arms 1a,1b of the flag yoke 1. In order to facilitate an accurate adjustment to the anatomical peculiarities of the patient, the supports can be configured so as to be adjustable.

This configuration of the fast transfer yoke can be used in particular in cases when due to patient conditions the earplugs cannot be used.

Figure 14:
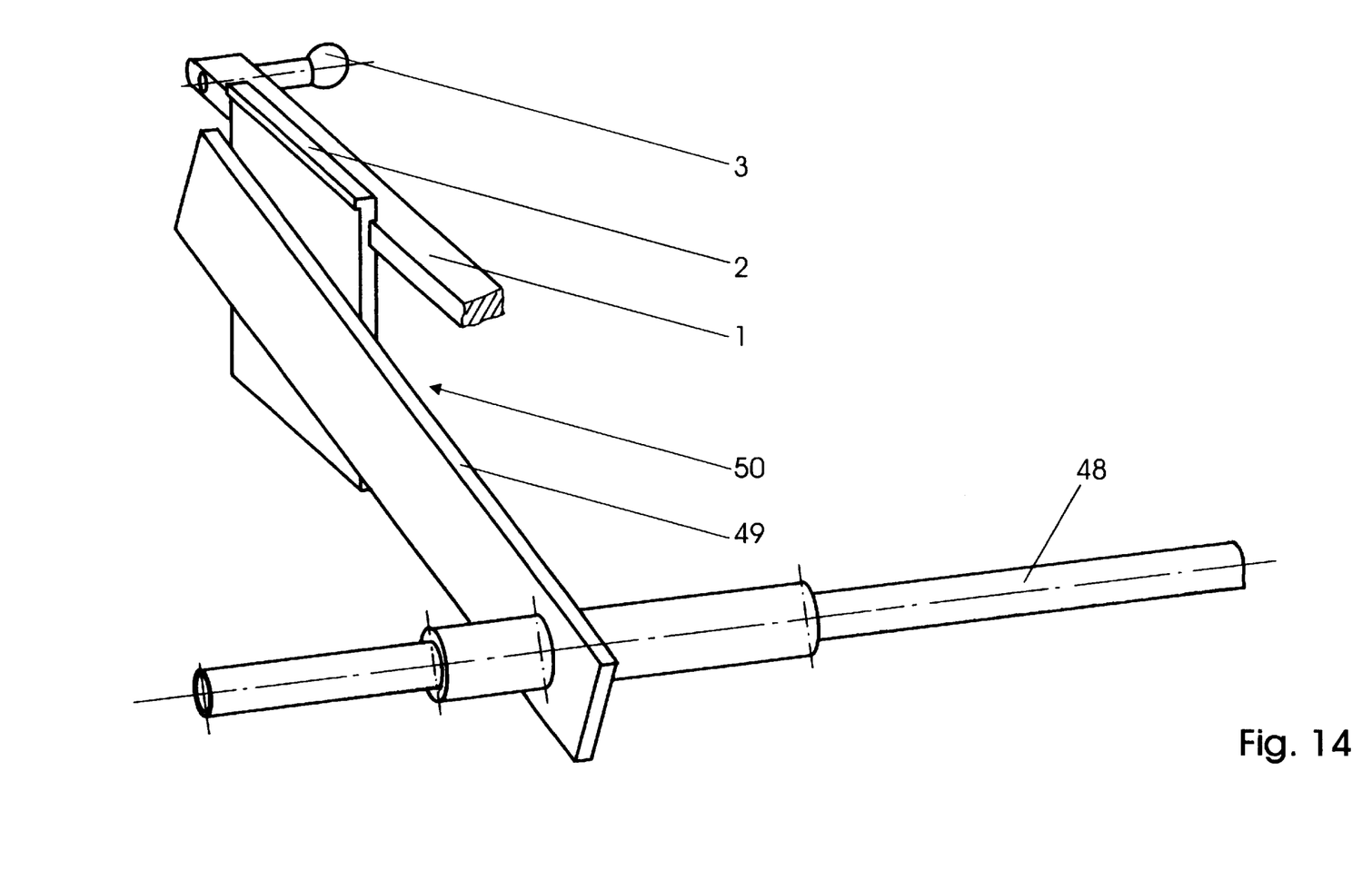
FIG. 14, a cross rod of the recording yoke with surfaces for the parallel attachment of the right and left lateral arms.

FIG. 14 shows another cross rod 48 of the recording yoke 21 with the lateral surfaces 50 on an adjusting arm 49 for a parallel attachment of the left and right lateral arm 54. This makes it possible to install the recording yoke 21 on the patient via the axis bore 10 in parallel with the flag yoke 1.

What is claimed is:

1. Fast transfer yoke for the cranium-calculated transfer of a plaster model of the maxilla from a patient into a dental articulator and for recording the geometry of an axis-related individual mandibular joint of the patient, the fast transfer yoke comprising:

a flag yoke adapted for attachment to the cranium of the patient and to a flag adapted to be located close to the mandibular joint, and an ear support adapted to be located in a fixed position with respect to an ear of the patient, and a glabella support adapted to be located in a fixed position with respect to the glabella of the patient for the stationary fixation on the cranium of the patient and a recording yoke having an occlusion fork adapted to be located in a fixed position with respect to the jaw of the patient and movable in response to mandiblery movement of the patient's jaw, and a write head located on the recording yoke and attached to the occlusion fork for actuation of the write head to record the mandiblery movement of the jaw;

the flag yoke (1) including a spring means (6) for the glabella support pressing against the glabella of the patient by means of spring force;

the flag (2) including an end piece (7) detachably connected with the flag yoke (1);

an angular plate (27) detachably attached to the flag;

the write head (22,22a) being positionable both on the flag (2) and on the angular plate (27), and a centering tip (20) positionable to the side of the flag (2) in an assumed or actual patient axis.

2. The fast transfer yoke according to claim 1 characterized in that the spring means is a rubber band (6) that straps the fast transfer yoke (1) to the cranium in a rearward direction.

3. The fast transfer yoke according to claim 1 characterized in that the flag (2) features an axis bore (10) in the position of the assumed patient axis.

4. The fast transfer yoke according to claim 3 including a mounting device (12) attachable to the flag yoke (1) for positioning centering tip (20) on the flag.

5. The fast transfer yoke according to claim 4 wherein the mounting device includes a carrier (18) that can be shifted longitudinally and that can be locked in position on the mounting device (12).

6. The fast transfer yoke according to claim 1 characterized in that the angular plate (27) is connected with the flag (2) by way of a clamping device (28).

7. The fast transfer yoke according to claim 6 characterized in that the clamping device (28) consists of a pressure plate (29) that is flush with the angular plate (27) and of a clamping jaw (30) that is positioned at a distance from the pressure plate (29) and that is pivotally connected with it.

8. The fast transfer yoke according to claim 7 characterized in that the clamping jaw (30) can be pivoted against a spring force in the direction toward the pressure plate (29).

9. The fast transfer yoke according to claim 1 characterized in that the angular plate (27) can be attached to the flag (2) by means of a magnetic mount (34).

10. The fast transfer yoke according to claim 1 characterized in that the angular plate (27) is attached directly to the arm of the flag yoke (1a,1b) or to the end pieces (7).

11. The fast transfer yoke according to claim 1 characterized in that the write head (22) is connected with the recording yoke (21) in a manner that makes it angularly rotatable by 90°, axially adjustable and exchangeable.

12. The fast transfer yoke according to claim 11 characterized in that the recording stylus (23) of the write head (22) is spring retained.

13. The fast transfer yoke according to claim 1 characterized in that the front end of the flag yoke (1) features a retaining device (38) for the retention of a writing plate (39) onto which a recording stylus (40) can be brought down that is adjustably attached to the handle (25) of the occlusion fork (26).

14. The fast transfer yoke according to claim 1 characterized in that a forehead support (51) can be attached to the flag yoke (1).

15. The fast transfer yoke according to claim 1 characterized in that flattened earplugs (31) are provided that are flattened in the direction of the glabella support (4).

16. The fast transfer yoke according to claim 1 characterized in that ear saddle supports (58) are provided that are attached by means of vertical supports (60) to end pieces (59) that are each assigned to a lateral arm (1a,1b) of the flag yoke (1).

17. The fast transfer yoke according to claim 16 characterized in that the end pieces (59) are each interchangeably attached to an arm (1a,1b).

18. The fast transfer yoke according to claim 17 characterized in that to the end piece (59) a flag (7) for mechanical or electronic recording of the joint path is attached.

19. The fast transfer yoke according to claim 16 characterized in that the ear saddle supports (58) can be height adjusted in relation to the flag yoke (1).

20. A fast transfer yoke for a cranium-calculated transfer of a maxilla plaster model of a patient into a dental articulator and for the recording of the axis-related individual mandibular joint geometry of the patient, the fast transfer yoke comprising:

a flag yoke (1) configured to be stationarily disposed adjacent the cranium of the patient so that the flag yoke (1) is adapted for pressing against the posterior wall of the acoustic meatus of the patient, the flag yoke (1) adapted for extending toward the mandibular joints of the patient;

an end piece (7) detachably connected to the flag yoke (1) and adapted for disposition adjacent the mandibular joints;

a sagittal flag (2) attached to the end piece (7) and adapted for disposition adjacent the mandibular joints of the patient;

an ear support (3) attached to the sagittal flag (2) and protruding therefrom, the ear support (3) configured to be inserted into the porus acusticus of the patient;

a glabella support (4) adjustably attached to the flag yoke (1) and adapted for extending toward the front of the cranium of the patient for stationary fixation on the cranium;

an angular plate (27) removably attached to the sagittal flag (2);

a write head (22, 22a) positioned on the sagittal flag (2) and the angular plate (27);

a recording yoke (21) for recording mandibular joint movement, the recording yoke (21) attached to the write head (22,22a) and adapted to extend therefrom toward the front of patient;

an occlusion fork (26) for the actuation of the write head (22,22a), the occlusion fork (26) being attached to the recording yoke (21) and adapted for extending toward the maxilla of the patient; and a centering tip (20) attached to the recording yoke and configured to be disposed adjacent the flag (2).

\* \* \* \* \*